(12) United States Patent
Penn

(10) Patent No.: US 8,918,160 B2
(45) Date of Patent: Dec. 23, 2014

(54) COMPUTER AIDED DIAGNOSTIC METHOD AND DEVICE

(76) Inventor: Alan Penn, Rockville, MD (US)

(*) Notice: Subject to any disclaimer, the term of this patent is extended or adjusted under 35 U.S.C. 154(b) by 155 days.

(21) Appl. No.: 13/542,315

(22) Filed: Jul. 5, 2012

(65) Prior Publication Data

US 2013/0012805 A1    Jan. 10, 2013

Related U.S. Application Data

(60) Provisional application No. 61/505,268, filed on Jul. 7, 2011, provisional application No. 61/642,207, filed on May 3, 2012.

(51) Int. Cl.
*A61B 5/05* (2006.01)
*A61B 5/055* (2006.01)
*G01R 33/563* (2006.01)

(52) U.S. Cl.
CPC .......... *A61B 5/055* (2013.01); *G01R 33/56341* (2013.01)
USPC ....................................... 600/411

(58) Field of Classification Search
CPC .......... G01N 24/00; G06T 2207/1008; G06T 2207/1092; G06T 2207/1096; A61B 5/055; A61B 6/03; Y10S 505/844; G01V 3/14; G01V 3/175; G01V 3/32; A61N 2005/1055; G01R 33/56341
USPC ....................................... 600/411
See application file for complete search history.

(56) References Cited

U.S. PATENT DOCUMENTS 7,974,676 B2    7/2011 Penn et al.
2007/0249931 A1    10/2007 Fain et al.
2010/0021035 A1    1/2010 Gupta et al.
2010/0081918 A1    4/2010 Sugiura et al.
2010/0298692 A1    11/2010 Schmainda et al.

FOREIGN PATENT DOCUMENTS

WO    2010116124    10/2010

OTHER PUBLICATIONS

Hosonuma et al., Clinical usefulness of diffusion-weighted imaging using low and high b-values to detect rectal cancer, Magn Reson Med Sci. Dec. 2006;5, 4:173-7.*
Kim et al., Diffusion-Weighted Imaging of Human Carotid Artery Using 2D Single-Shot Interleaved Multislice Inner Volume Diffusion-Weighted Echo Planar Imaging (2D ss-IMIV-DWEPI) at 3T: Diffusion Measurement in Atherosclerotic Plaque, Journal of Magnetic Resonance Imaging 30:1068-1077, 2009.*

(Continued)

*Primary Examiner* — Long V Le
*Assistant Examiner* — Bo J Peng
(74) *Attorney, Agent, or Firm* — Browdy and Neimark, PLLC

(57) ABSTRACT

A method for generating a map of a region of a patient's body containing one or more lesions that provides information about MR diffusion properties and/or level of suspicion of malignancy. Performing at least one first scan of the region with an MRI apparatus set to a first b value to obtain a first matrix of pixel or voxel values, $int(B_1)$; performing at least one second scan of the region with the apparatus set to a second b value to obtain a second matrix of pixel or voxel intensity values, $int(B_2)$; deriving a first computed value that is a monotonic function of $\ln(int(B_1)/int(B_2))$; multiplying each computed value by a value proportional to $int(B_1)$ to obtain a second computed value; and producing a representation of all the second computed values that is indicative of the likelihood that one or more of the lesions are malignant.

9 Claims, 4 Drawing Sheets

(56) References Cited

OTHER PUBLICATIONS

Eyal et al., "A Novel MRI method for Breast Cancer Detection Based on Diffusion Tensor Tracking of the Ductal Tree." Paper C-0329. Proc ISMRM 19, May 2010.

Partridge et al., "Diffusion Tensor MRI: Preliminary Anisotropy Measures and Mapping of Breast Tumors," Journal of Magnetic Resonance Imaging, Feb. 2010, 31:339-347.

Koh et al., "Diffusion-Weighted MRI in the Body: Applications and Challenges in Oncology." AJR Jun. 2007; 188:1622-1635.

Partridge et al., "Differential Diagnosis of mammographically and Clinically Occult Breast Lesions on Diffusion-Weighted MRI." Journal of Magnetic Resonance Imaging, Mar. 2010, 31:562-570.

Guo et al., "Differentiation of Clinically Benign and Malignant Breast Lesions using Diffusion-Weighted Imaging," Journal of Magnetic Resonance Imaging, 2002, 16:172-178 (2002).

Yili et al., "The value of diffusion-weighted imaging in assessing the ACD changes of tissues adjacent to breast carcinoma." BMC Cancer Jan. 14, 2009, 9:18: 1-10. (available at http://www.biomedcentral.com/1471-2407/9/18).

Jones et al., "Optimal strategies for measuring diffusion in anisotropic systems by magnetic resonance imaging," Magn Reson Med 1999; 42:515-525.

Partridge et al., "Quantitative Diffusion-Weighted Imaging as an Adjunct to Conventional Breast MRI for Improved Positive Predictive Value," AJR Dec. 2009; 193-1716-1722.

Graessner, "Frequently Asked Questions: Diffusion Weighted Imaging (DWI)," available at: http://www.medical.siemens.com/siemens/it_IT/gg_mr_FBAs/files/MAGNETOM_World/Application_Tips/MAGNETOM_Flash_46/Frequently_Asked_Questions_Diffusion-Weighted_Imaging.pdf, Jan. 2011.

Charles-Edward et al., "Diffusion-weighted magnetic resonance imaging and its application to cancer," Cancer Imaging (2006),6. 135-143.

Quantitative MRI of the Brain, Chapter 7, pp. 204-218 (P. Tufts ed., John Wiley & Sons, Ltd. 2003, ISBN: 0-470-84721-2.

Kuroki et al., "Diffusion-weighted Imaging of Breast Cancer with the Sensitivity Encoding Techniques: Analysis of the Apparent Diffusion Coefficient Value," Magnetic Resonance in Medical Sciences, vol. 3, No. 2, p. 79-85: 2004.

Baltzer et al., "Diffusion Tensor magnetic Resonance Imaging of the Breast: A Pilot Study," Eur Radiol, published online Jul. 29, 2010. In print.

Partridge et al., "Apparent Diffusion Coefficient Values for Discriminating Benign and Malignant Breast MRI Lesions: Effects of Lesion Type and Size." AJR, vol. 194, Jun. 2010; 1994:1664-1673.

Yili et al., "The value of diffusion-weighted imaging in assessing the ACD changes of tissues adjacent to breast carcinoma." BMC Cancer, Jan. 14, 2009, 9:18: 1-10. (available at http://www.biomedcentral.com/1471-2407/9/18).

Penn et al., Morphologic Blooming in Breast MRI as a Characterization of Margin for Discriminating Benign from Malignant Lesions. Acad Radiol 2006; 13:1344-1354.

Partridge et al., "Improved Diagnostic Accuracy of Breast MRI Through Combined Apparent Diffusion Coefficients and Dynamic Contrast-Enhanced Kinetics." Magnetic Resonance in Medicine 65:1759-1767, published online Jan. 19, 2011.

Sinha et al., "In vivo diffusion-weighted MRI of the breast: potential for lesion characterization." J Magn Reson Imaging 2002;15:693-704.

Bogner et al., "Diffusion-weighted MR for differentiation of breast lesions at 3.0 T: how does selection of diffusion protocols affect diagnosis?" Radiology 2009;253:341-351.

Le Bihan et al., "Separation of diffusion and perfusion in intravoxel incoherent motion MR imaging." Radiology 1988;168:497-505.

Hatakenaka et al, "Apparent Diffusion Coefficients of Breast Tumors: Clinical Application," Magn Reson med Sci, 7 (1), pp. 23-29 (2008)).

Toyoda, et al. "Usefulness of high-b-value diffusion-weighted imaging in acute cerebral infarction," Eur Radiol (2007) 17:1212-1220.

Guangwei et al., The Role of Parallel Diffusion-Weighted Imaging and Apparent Diffusion Coefficient (ADC) Map Values for Evaluating Breast Lesions: Preliminary Results. NIH Public Access Author Manuscript Acad Radiol. Author manuscript; available in PMC Apr. 1, 2011.

\* cited by examiner

ADC AND HADAMARD IMAGES OF SAME ROI CONTAINING MALIGNANT BREAST LESION

HADAMARD IMAGE

UNIDIRECTIONAL ADC MAP

MALIGNANT LESION APPEARS AS LIGHT REGION WITH UNSHARP (LOW GRADIENT) BORDER, AN INDICATION OF CANCER, ON HADAMARD IMAGE.

MALIGNANT LESION DOES NOT APPEAR AS DARK REGION, THE MARKER FOR CANCER ON ADC MAP. BORDER IS INDISTINGUISHABLE.

COMPUTER AIDED DIAGNOSTIC METHOD AND DEVICE

This invention was made with U.S. Government support under contract number HHSN261201100075C awarded by National Institutes of Health (NIH). The U.S. Government has certain rights in the invention.

BACKGROUND OF THE INVENTION

The present invention relates to a method and device for estimating the likelihood that an image of a body or body part obtained through Diffusion Tensor Imaging (DTI) or Diffusion Weighted Imaging (DWI) contains a lesion and further estimating the likelihood that the lesion is cancer.

The known technique of diffusion imaging is disclosed in U.S. Patent Application Publication No. 20100298692A1, the disclosure of which is incorporated herein by reference.

Background in breast MRI methods and terminology: The invention is applicable to a plurality of parts of the body. For the sake of clarity, the background and description will be described in terms of detection and diagnosis of breast cancer. It is to be understood that this description is for illustrative purposes and does not restrict the field of application to any specific form of cancer or any specific part of the body.

Diffusion Tensor Imaging (DTI) measures the magnitude and direction of random motion of water molecules and requires the acquisition of signals in at least 6 directions. If the random motion is assumed to be isotropic, then a simplified form of DTI, called Diffusion Weighted Imaging (DWI) can be used, which only requires acquisition of signal in 3 directions. A qualitative representation of a diffusion image can be obtained using a single direction.

The physiological basis of using DWI/DTI for cancer diagnosis is that the densely packed cells within a cancer restrict the normal random motion (Brownian motion) that occurs within all cells. A low level of random motion within the cells is an indicator of cancer which is different from the vascularization characterized by dynamic contrast imaging (DCE), the current standard for breast MR detection and diagnosis. The most common diagnostic values obtained from diffusion analysis are:

1. The apparent diffusion coefficient (ADC): an aggregate measure of the degree of diffusion that can be derived from the three directions used for DWI. ADC maps can be used by radiologists to distinguish areas with low Brownian motion that are suspicious for cancer. Areas of low ADC values are suspicious for breast cancer because the may indicate high cellular, low diffusion region within a malignant lesions. [Eyal E., Shapiro-Feinberg M., Furman-Haran E., Grobgeld D., Golan T., Itzchak Y, Catane R, Papa M., Degani H. "A Novel MRI method for Breast Cancer Detection Based on Diffusion Tensor Tracking of the Ductal Tree." Paper C-0329. Proc ISMRM 19, May 2010]
2. Fractional anisotropy (FA): an aggregate measure of anisotropy that requires the six or more directions used for DTI. FA maps can be used by radiologists to distinguish areas of strong and weak anisotropy.

The following gives a summary of the use of tensor eigenvalues as applied to diffusion MR imaging:

Apparent diffusion coefficient (also known as the mean diffusivity, $D_{av}$) describes the degree of mobility or restriction of water molecules, and is given by $$ADC = (\lambda_1 + \lambda_2 + \lambda_3)/3 \text{ mm}^2/\text{second},$$

where $\lambda 1, \lambda 2, \lambda 3$ are the maximum, intermediate, and minimum diffusion tensor eigenvalues, respectively. The eigenvalues describe the magnitude or rate of diffusion along each of the three principal axes of the diffusion tensor ellipsoid (in mm$^2$/second).

Fractional anisotropy is a unitless measure of the degree of directionality of intravoxel diffusivity, calculated by $$FA = \frac{\sqrt{[(\lambda_1 - \lambda_2)^2 + ((\lambda_2 - \lambda_3)^2 + ((\lambda_1 - \lambda_3)^2]}}{\sqrt{2}\sqrt{[\lambda_1^2 + \lambda_2^2 + \lambda_3^2]}}$$

"For isotropic diffusion ($\lambda 1 = \lambda 2 = \lambda 3$), FA is zero, and in the case of high anisotropy where there is a strongly preferred direction of diffusion $\lambda 1 \gg \lambda 2 > \lambda 3$". [Partridge, S C, Ziadloo A, Murthy R, White S W, Peacock S, Eby P R, DeMartini W B, Lehman C D. "Diffusion Tensor MRI: Preliminary Anisotropy Measures and Mapping of Breast Tumors," Journal of Magnetic Resonance Imaging, February 2010, 31:339-347]

The sensitivity of the DWI sequence to water motion can be varied by changing the gradient amplitude, the duration of the applied gradient, and the time interval between the paired gradients. On clinical MR scanners, the diffusion sensitivity is easily varied by changing the parameter known as the "b" value, which is proportional to these three factors. When the b value is changed, it is usually the gradient amplitude, rather the duration or time intervals between gradients, that is altered. [Koh D-M, Collins DJ. "Diffusion-Weighted MRI in the Body: Applications and Challenges in Oncology." AJR June 2007; 188:1622-1635]

The ADC map can be computed from the DWI or DTI data using at least two different b values. When the ADC value is computed using two b values, the following equation is used, where $S_{DWI}$ is the combined DWI (geometric average of unidirectional high b diffusion-weighted images), and $S_0$ is the T2-weighted b=0 s/mm$^2$ reference image. [Partridge, S C, DeMartini W B, Kurland B F, Eby P R, White S W, Lehman C D. "Differential Diagnosis of mammographically and Clinically Occult Breast Lesions on Diffusion-Weighted MRI." Journal of Magnetic Resonance Imaging, Mar 2010, 31:562-570]

$$ADC = -\frac{1}{b}\ln\left(\frac{S_{DWI}}{S_0}\right)$$

High b value of 1000 has been used by some researchers [Guo Y, Cai Y-Q, Cai Z-L, Gao Y-G, An N-Y, Ma L, Mahankali S, Gao, J-H. "Differentiation of Clinically Benign and Malignant Breast Lesions using Diffusion-Weighted Imaging," Journal of Magnetic Resonance Imaging, 2002, 16:172-178 (2002)], [Yili Z, Xiaoyan H, Hongwen D, Yun Z, Xin C, Peng W, Youmin G. "The value of diffusion-weighted imaging in assessing the ACD changes of tissues adjacent to breast carcinoma." BMC Cancer 2009, 9:18: 1-10. (available at http://www.biomedcentral.com/1471-2407/9/18)], while Partridge, et al have used a high b value of 600, noting that:

"It has been shown that the b-value that provides the highest signal-to-noise ratio for a spin-echo diffusion-weighting sequence is equal to 1.1/ADC [citing [Jones D K, Horsfield M A, Simmon A. "Optimal strategies for measuring diffusion in anisotropic systems by magnetic resonance imaging," Magn Reson Med 1999; 42:515-525.]] For breast imaging, with typical reported ADC values of 1.6-2.0×10³ mm²/s for normal tissue, this corresponds to an optimal diffusion weighting of approximately b=600 s/mm²." Partridge, S C, DeMartini W B, Kurland B F, Eby P R, White S W, Lehman C D. "Quantitative Diffusion-Weighted Imaging as an Adjunct to Conventional Breast MRI for Improved Positive Predictive Value," AJR December 2009; 193-1716-1722].

Non-zero low values of b, such as b=100, are sometimes used in place of b=0.

The selection of a low b-value larger than zero provides suppression of large vessels which makes lesions more conspicuous. The calculation of the tissue ADC can be more accurate when starting with even higher b-values like 100 or 200 to omit the contribution of flow and microvascular effects.

[Graessner, "Frequently Asked Questions: Diffusion Weighted Imaging (DWI)," available at: http://www.medical-.siemens.com/siemens/it_IT/gg_mr_FBAs/files/MAGNE-TOM_World/Application_Tips/MAGN ETOM_Flash_46/ Frequently_Asked_Questions_Diffusion-Weighted_Imaging.pdf].

Clinical MR systems generate diffusion weighted images in three directions, typically slice, frequency (read) and phase encoded. [Charles-Edwards E and deSousa, N, "Diffusion-weighted magnetic resonance imaging and its application to cancer," Cancer Imaging (2006),6. 135-143] The minimum number of scans to obtain the ADC from the three orthogonal directions is 4: one scan at b=0 plus three unidirectional scans at high b value taken in the three orthogonal directions. ["D: the Diffusion of Water" (Chapter 7), Wheeler-Kingshott, et al. from: Quantitative MRI of the Brain (P. Tufts ed., 2003, John Wiley & Sons, Ltd. ISBN: 0-470-84721-2]

DCE and DWI/DTI measure different physiological characteristics and can provide complementary information.

Images derived from DCE sequences are used to evaluate the enhancement pattern of a contrast agent (gadolinium) into and out of a lesion. Clinical evaluation is based on both the shape of the enhancement pattern (morphology) and the rate of flow of the contrast agent into and out of the lesion (kinetics). Both morphology and kinetics provide information about the vascularization that feeds the lesion; the physiological rationale for DCE is that cancerous lesions require increased vascularization to feed the growing tumor. Increased vascularization indicated by morphological and kinetic patterns of the contrast agent is regarded as a suspicious marker.

Images derived from DWI/DTI characterize random motion within cells as an indicator of cellular density.

Clinical advantages and problems associated with DWI are summarized as follows:

Dynamic contrast enhanced (DCE) MRI is used for detection and diagnosis of breast cancer only for special cases, presumably because of its relatively high costs, significant false positive rates, discomfort and risk of adverse effects, including nephrogenic systemic fibrosis. Recently, it was shown that apparent diffusion coefficient (ADC) values can help distinguish between cancers, benign lesions and normal breast tissue. However, ADC maps are not sufficiently sensitive for establishing a stand alone method for breast cancer detection. [Eyal E., Shapiro-Feinberg M., Furman-Haran E., Grobgeld D., Golan T., Itzchak Y, Catane R, Papa M., Degani H. "A Novel MRI method for Breast Cancer Detection Based on Diffusion Tesor Tracking of the Ductal Tree." Paper C-0329. Proc ISMRM, 19, May 2010].

MRI advances, including parallel imaging, have enabled improvement in DWI utility:

The usefulness of DWI has already been established in the field of neuroradiology. Despite its excellent contrast resolution, DWI has the disadvantages of susceptibility and chemical shift artifacts. The introduction of the latest parallel imaging techniques, represented by SENSE technique, has solved these problems and enabled DWI to produce images clinically acceptable not only for neuroradiology but also for a variety of other fields. This is probably because the parallel imaging techniques are capable of reducing the number of phase encoding steps and the time required to fill the k-space, which may lead to the suppression of susceptibility and chemical artifacts. [Kuroki, Y, Nasu K, Kuroki S, Murakami K, Hayashi, T, Sekiguchi R, Nawano S. "Diffusion-weighted Imaging of Breast Cancer with the Sensitivity Encoding Techniques: Analysis of the Apparent Diffusion Coefficient Value," Magnetic Resonance in Medical Sciences, Vol. 3, No. 2, p. 79-85: 2004].

One inherent problem with breast DCE, the current standard method of magnetic resonance imaging, is that enhancing agents are routinely used off-label. Non-labeled use can result in inconsistency in how the contrast agent is administered. An important advantage of DWI/DTI is that it does not require an enhancing agent and problems associated with administration of the agent do not exist.

In spite of limited sensitivity of ADC maps, the information provided by ADC maps has the potential to lead to improved detection and diagnosis of breast cancer. In some cases, such as those in which the patients cannot tolerate the enhancing agent or where the high cost of acquiring enhanced images precludes their clinical application, DWI could provide an alternative to DCE.

One reported advantage of DWI over DCE is that diagnostic performance of DWI is similar for mass and non-mass-like enhancement type lesions and may be higher for smaller (<1 cm) versus larger lesions. [Partridge, S C, DeMartini W B, Kurland B F, Eby P R, White S W, Lehman C D. "Quantitative Diffusion-Weighted Imaging as an Adjunct to Conventional Breast MRI for Improved Positive Predictive Value," AJR, December 2009; 193:1716-1722].

Moreover, DWI was found to perform equally well on invasive ductal and invasive lobular carcinoma. [Partridge, S C, DeMartini W B, Kurland B F, Eby P R, White S W, Lehman C D. "Quantitative Diffusion-Weighted Imaging as an Adjunct to Conventional Breast MRI for Improved Positive Predictive Value," AJR December 2009; 193:1716-1722].

One primary reasons that DWI/DTI cannot currently be used in place of DCE for breast cancer screening is overlap of DWI intensity between benign and malignant lesions:

"However, because of considerable overlap in ADC of benign and malignant lesions, breast DWI must remain as a research tool until larger studies are performed to validate these findings."

[Partridge, S C, DeMartini W B, Kurland B F, Eby P R, White S W, Lehman C D. "Quantitative Diffusion-Weighted Imaging as an Adjunct to Conventional Breast MRI for Improved Positive Predictive Value," AJR, December 2009; 193:1716-1722].

Overlap of benign and malignant lesions can be mitigated by the use of features that supplement the discrimination realized from analysis of differences in pixel intensity values on ADC map, as is presently done. Partridge and Baltzer investigated one such feature, fractional anisotropy (FA). Baltzer showed the following results of FA analysis of breasts.

"FA values of parenchyma were higher than those of benign lesions but at the same level of those of malignant lesions." [Baltzer PAT, Schafer A, Dietzel M, Grassel D, Gajda M, Camara O, Kaiserr W A. "Diffusion Tensor magnetic Resonance Imaging of the Breast: A Pilot Study," Eur Radiol, published online Jul. 29, 2010. In print]

DWI can be acquired with a shorter acquisition time than is required for a DCE procedure that involves precontrast imaging, administration of contrast agent and saline push, and a sequence of dynamic contrast images that stretch over several minutes. In published literature, Partridge reported diffusion acquisition time of 2:40 minutes in both her DWI [and DTI studies. Partridge's DWI images were acquired using six directions. [Partridge, S C, Mullins C D, Kurland B F, Allain M D, DeMartini W B, Eby P R, Lehman C D. "Apparent Diffusion Coefficient Values for Discriminating Benign and Malignant Breast MRI Lesions: Effects of Lesion Type and Size." AJR June 2010; 1994:1664-1673] [Partridge, S C, Ziadloo A, Murthy R S, White S W, Peacock S, Eby PR, DeMartini W B, Lehman C D. "Diffusion Tensor MRI: Preliminary Anisotropy Measures and Mapping of Breast Tumors," Journal of Magnetic Resonance Imaging February 2010, 31:339-347]

The scientific basis of the proposed invention is based on two published results:

1. Study reported by Yili, et al., found that ADC values within 5 mm of a malignant lesion have cancer-like attributes, and that these cancer-like attributes tend to disappear as you move further from the lesion.[Yili Z, Xiaoyan H, Hongwen D, Yun Z, Xin C, Peng W, Youmin G. "The value of diffusion-weighted imaging in assessing the ACD changes of tissues adjacent to breast carcinoma." BMC Cancer 2009, 9:18: 1-10. (available at http://www.biomedcentral.com/1471-2407/9/18)]
2. A study directed by the inventor that demonstrated that the sharpness of the margin or gradient of a breast lesion on MRI discriminates benign from malignant conditions.[Penn A I, Thompson S F, Brem R F, Lehman C, Weatherall P, Schnall M D, Newstead G M, Conant, E F Ascher S M, Morris E, Pisano E D. Morphologic Blooming in Breast MRI as a Characterization of Margin for Discriminating Benign from Malignant Lesions. Acad Radiol 2006; 13:1344-1354.]

"Others have shown that the signal loss from diffusion in vivo is driven by both perfusion and diffusion, with the changes at low b values dominated by perfusion and the higher values characterizing intra- and extra-cellular diffusion (17,39,40)." [S. C. Partridge, H. Rahbar, R. Murthy, X. Chai, B. F. Kurland, W. B. DeMartini, and C. D. Lehman. "Improved Diagnostic Accuracy of Breast MRI Through Combined Apparent Diffusion Coefficients and Dynamic Contrast-Enhanced Kinetics." Magnetic Resonance in Medicine 65:1759-1767 (2011)].

Cited references in above quote:

17. Sinha S, Lucas-Quesada FA, Sinha U, DeBruhl N, Bassett LW. In vivo diffusion-weighted MRI of the breast: potential for lesion characterization. J Magn Reson Imaging 2002;15:693-704.

39. Bogner W, Gruber S, Pinker K, Grabner G, Stadlbauer A, Weber M, Moser E, Helbich TH, Trattnig S. Diffusion-weighted MR for differentiation of breast lesions at 3.0 T: how does selection of diffusion protocols affect diagnosis? Radiology 2009;253:341-351.

40. Le Bihan D, Breton E, Lallemand D, Aubin ML, Vignaud J, Laval-Jeantet M. Separation of diffusion and perfusion in intravoxel incoherent motion MR imaging. Radiology 1988;168:497-505.

BRIEF SUMMARY OF THE INVENTION

The present invention operates on maps or images generated from Diffusion MR image data sets that may contain benign or malignant lesions. Benign and malignant lesions can be found in many parts of the body.

One feature of the invention is implemented by a method for generating a map of a region of a patient's body that provides information about the nature of lesion(s) in the region, the region being composed of a two or three dimensional matrix of elemental subregions, the method comprising:

performing at least one first scan of the region with an MRI apparatus set to a first b value, $B_1$, to obtain a first matrix of pixel or voxel intensity values, int $(B_1)$, each intensity value being derived from a respective subregion;

performing at least one second scan of the region with the MRI apparatus set to a second b value, $B_2$, to obtain a second matrix of pixel or voxel intensity values, int $(B_2)$, each intensity value being derived from a respective volume subregion;

deriving, for each subregion, a first computed value that is a logarithmic function of (int $(B_1)$/int$(B_2)$) or a monotonic function of ln (int $(B_1)$/int$(B_2)$);

multiplying each computed value by a value proportional to int $(B_1)$ for the same subregion to obtain a second computed value for each subregion; and producing a representation of all the second computed values.

To cite one example, if $B_1=0$, then only one $B_1$ scan is needed and the results of that scan are paired with the results of the $B_2$ scan that may be different for the scan in each direction. If $B_1>0$, then the same $B_1$ value is used for each direction and the results of the $B_1$ scan is paired with the corresponding results of the $B_2$ scan for each direction.

Herebelow, $B_1$ will be referred to as $B_{low}$ and $B_2$ will be referred to as $B_{high}$.

Another feature of the invention is implemented by a method for characterizing regions on a map or image generated from diffusion image data of a region of a patient's body, comprising:

loading into a data processing device image data achieved by calculation from MR diffusion imaging;

providing a first threshold level to distinguish pixels with image data values that are above or below the values found that are not representative of pathological portions of the region of the patient's body;

providing a second threshold level that is higher than the first threshold;

deriving a measure related to the gradient pattern of those pixels that lie within a margin zone defined by those pixels that satisfy a criterion of the second threshold but do not satisfy a criterion of the first threshold and;

outputting the measure related to the gradient as a parameter indicative of the likelihood that the pixels that are within the margin zone and/or a region related to the margin zone are cancerous.

DETAILED DESCRIPTION OF THE INVENTION

Figure 1:
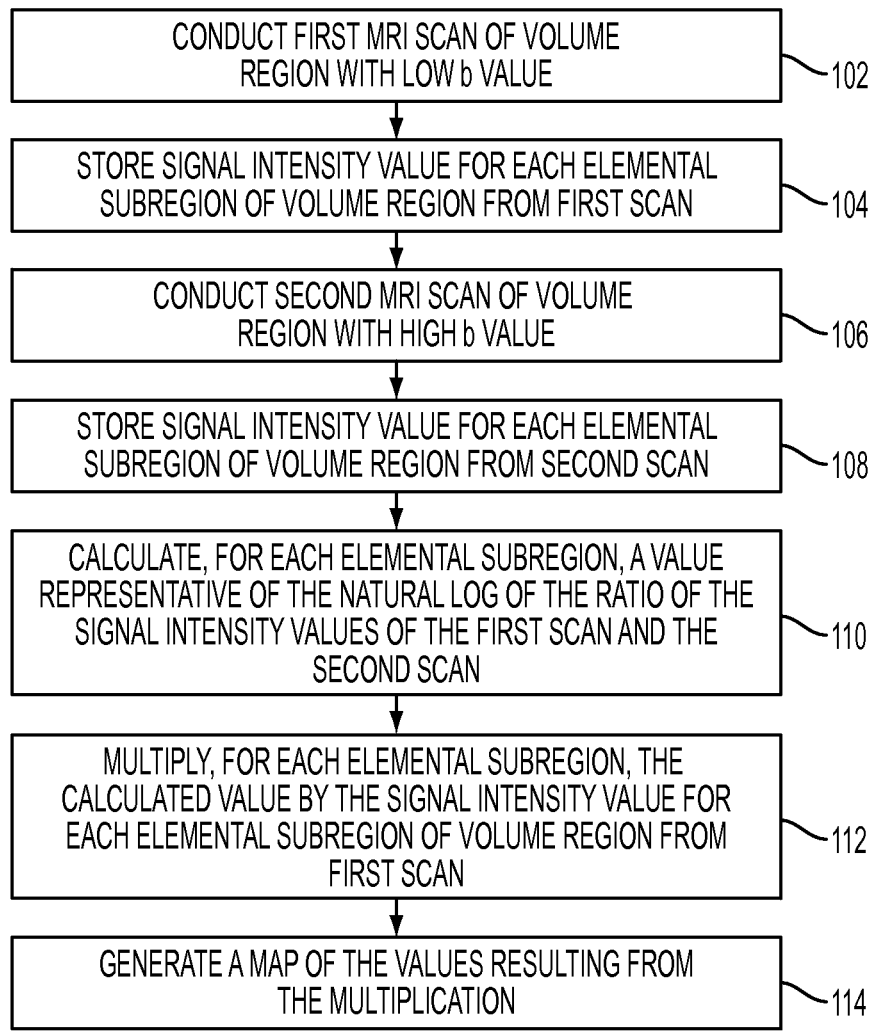
FIG. 1 is a programming diagram showing the basic steps for generating a map or image according to the present invention.

Published studies on breast diffusion imaging have reported that 10%-20% of test cases could not be evaluated because of problems related to the quality of the ADC images. For example, Hatakenaka ("Apparent Diffusion Coefficients of Breast Tumors: Clinical Application," Magn Reson med Sci, 7(1), pp 23-29 (2008)) reported that "34 [of 179] cases were excluded as a result of small lesions and/or poor visualization of the lesions on DWI," and Partridge (Diffusion Tensor MRI: Preliminary Anisotropy Measures and Mapping of Breast Tumors," J Mag Res Imag 31, pp 339-347 (2010)) reported that "19 [of 158 lesions] were excluded because of technical problems with the DTI sequence—misregistration (N=15), poor fat suppression (N=2), or incomplete coverage of the lesion (N=2)."

The present invention provides a method and device that uses diffusion data to generate alternative images to ADC images for the detection and evaluation of possibly cancerous lesions.

The method and device and device according to this invention creates one or more novel maps generated from magnetic resonance diffusion scan data, image data sets that may contain benign or malignant lesions, so that computer programs, including the invention disclosed herein and in prior provisional application, and/or radiologists, including situations where a radiologist pre-reviews cases to determine which cases should have computer analysis, are able to better detect the presence of malignant lesions and/or discriminate malignant lesions from benign lesions when compared to the performance on the ADC maps. The novel maps may be in the form of a matrix of pixel or voxel values corresponding to spatial locations of pixel or voxel values in the ADC maps or in the form of paper or computer output generated from the matrix of pixel or voxel values suitable for either visual or computer analysis.

Common usage of the term "ADC" refers to a matrix of pixel or voxel values derived from three directional scans in the case of DWI and six or more scans in the case of DTI. However, the term "ADC" is also used to describe a map generated from a single unidirectional scan. *Quantitative MRI of the Brain* (P. Tufts ed., 2003, John Wiley & Sons, Ltd. ISBN: 0-470-84721-2 contains the following description of diffusion along a specific direction:

"The PFG (Pulsed Field Gradient) method can be included in most MRI sequences to introduce diffusion weighting along a specific direction (given by the direction along which the diffusion gradient is applied). This gives a reduced signal in areas of the sample where the self-diffusion coefficient in that direction is higher."

"If S(TE,0) and S(TE,b), together with the value of the b-factor, are known for each voxel of the imaged slice, a voxel-by-voxel calculation using Equation (7.16) [the Stejskal-Tanner formula] can produce a diffusion map, where each voxel value is the average diffusion coefficient of the tissue contained in that voxel, measured along the direction of application of the diffusion gradient." FIG. 7.6 of the same book shows an example of "ADC maps along x, y, and z [directions]."

In this citation, S is the signal value, TE is echo time of the pulse sequence, 0 is representative of the low b-value, and "b" is representative of a high non-zero b-value Since the unidirectional-ADC does not require multiple scans in different directions, images are not degraded by misregistration resulting from patient movement between scans, and time consuming registration programs to correct for patient motion are not needed.

Herein, we refer to ADC derived from a single directional scan as "unidirectional-ADC." The unidirectional-ADC values, computed from the matrix of signals for a single direction, is proportional to the $\ln(\text{int}(B_{low})/\text{int}(B_{high}))$, where int $(B_{low})$ is the intensity of the pixel value(s) computed using $b=B_{low}$, and $\text{int}(B_{high})$ is the intensity of the pixel value(s) computed using $b=B_{high}$. $B_{low}$ and $B_{high}$ are two specific b values selected by the operator.

Equivalently, the unidirectional-ADC values are proportional to the values consisting of $\{\ln(\text{int}(B_{low}))-\ln(\text{int}(B_{high}))\}$. Frequently $B_{low}$ is set equal to 0, as in the description and quotations given above, but for some applications, a positive value of $B_{low}$, say $B_{low}=100$, may be used. Images derived from the matrix $\{\ln(\text{int}(B_{low}))-\ln(\text{int}(B_{high}))\}$ frequently lack conspicuity of lesions in the images. Since lesions are generally conspicuous in the $B_{low}$ image, it is the purpose of the invention to make the lesions more conspicuous by multiplying every pixel or voxel of $\{\ln(\text{int}(B_{low}))-\ln(\text{int}(B_{high}))\}$ by the value of the corresponding pixel or voxel in, preferably, the $B_{low}$ image. The mathematical operation of combining two matrices by multiplying their corresponding elements is known as the Hadamard operation, and the resultant matrix is referred to in this disclosure as the "Hadamard image."

"High-b-value DWI using a clinical magnetic resonance imaging (MRI) system has been applied and clinical benefit of it has been discussed in the diagnosis of cerebral infarction [3-5], tumorous lesions [5] and degenerative diseases in recent years. However, an increase of the b-value results in a longer echo time (TE), and also decreases the signal-to-noise ratio (SNR) attributed to enlargement of the field of view (FOV). Initial application of DWimaging with high b-values of 2,500-3,000 s/mm2 for acute or subacute infarction provided no apparent diagnostic advantages compared with those of usual b=1,000 s/mm2 images [3, 4]. " [Toyoda, et al. "Usefulness of high-b-value diffusion-weighted imaging in acute cerebral infarction," Eur Radiol (2007) 17:1212-1220.]

The present invention thus provides an improved method and device for creating maps generated from diffusion image data that may contain cancerous lesions so that a radiologist and/or a set of computer instructions is better able to detect the existence of cancerous lesions and/or discriminate benign from cancerous lesions with a higher degree of accuracy than the radiologist and/or set of computer instructions could achieve using ADC maps.

To accomplish this, the present invention is characterized by a method and a device for generating novel maps that can be used in place of ADC maps as source data in steps performed by either the radiologist or a computer for the purpose of detecting cancerous lesions and/or discriminating benign from malignant lesions. This method comprises the following steps:

1) Selecting two or more "b" values for computation of ADC as described above, one of which is denoted in this disclosure as "high-b" and one of which is denoted in this disclosure as "low-b."

2) Loading an ADC image resulting from unidirectional scanning and produced by calculation from diffusion scan data for the high-b, such image referred to in this disclosure as "ADChigh," and loading an ADC image obtained by unidirectional scanning in the same direction and produced by calculation from diffusion scan data for the low-b, such image referred to in this disclosure as "ADClow," where ADChigh and ADClow are matrices having the same dimensions.

3) Deriving a unidirectional image in one-to-one correspondence with ADChigh wherein each pixel or voxel of the derived image is the natural log of the pixel or voxel value of ADChigh, where the derived image is denoted in this disclosure as "lnADChigh," and deriving a unidirectional image in one-to-one correspondence with ADClow wherein each pixel or voxel of the derived image is the natural log of the pixel or voxel value of ADClow, where the derived image is denoted in this disclosure as "lnADClow," While the invention is disclosed in terms of the natural log, it is understood that log to another numerical base, discretized approximations of the ln, or other mathematical functions could also be similarly used to achieve the same purpose.

4) Deriving a second image or set of images in one-to-one correspondence with ADChigh and ADClow by subtracting the pixel values of lnADClow from lnADChigh or lnADChigh from lnADClow and then multiplying the result of every subtracted element by the corresponding value of ADClow. The third image or set of images is referred to in this disclosure as the "Hadamard Image" or the "Hadamard Images."

5) Using the Hadamard Image or Hadamard Images, or data derived from the Hadamard Image or Hadamard Images, as the source data for visual or computer interpretation in one or more steps in which the ADC image, or data from the ADC image can be used to detect cancerous lesions or to discriminate cancerous from benign lesions.

One example of this procedure is shown in FIG. 1. In step 102, a first MRI scan of the volume region is carried out with a low b value. In step 104, a signal intensity value for each elemental subregion of the volume region from first scan is stored. In step 106, MRI scan of the volume region is carried out with a high b value. In step 108, a signal intensity value for each elemental subregion of the volume region from second scan is stored. In step 110, for each elemental subregion, a value representative of the difference between the signal intensity values from the first scan and the second scan is calculated. In step 112, for each elemental subregion, the calculated value is multiplied by the signal intensity value for each elemental subregion of volume region from first scan. Finally, in step 114, a map or image of the values resulting from the multiplication is generated.

Alternatively, the high-b and/or low-b scan values may be generated from the same physical scan on the MRI equipment.

The present invention provides radiologists and/or follow-up post-processing computers with an additional feature in the form of an indication of suspicion computed from the ADC map or the Hadamard image that is different from the evaluation of pixel intensity values.

In a study using the above-described procedure, two scans were performed in a primary plane of acquisition; the primary plane in the study was axial, but it could be coronal or sagital. Each scan was processed independently, producing for each scan a measure of suspicion. A conclusion was then based on the maximum of the measures for the two scans.

The diffusion scans could actually be performed after a dynamic contrast series while contrast agent is still in the volume region being observed. However, the calculations according to the present invention are independent of whether or not contrast agent is present.

Figure 2:
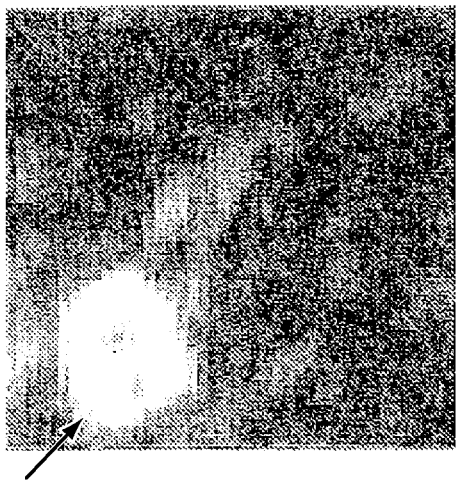
FIG. 2 is a representation of images demonstrating the improvement according to the present invention.
Figure 2:

FIG. 2 shows a unidirectional ADC image and a corresponding Hadamard image for a section of a human female breast that contains a malignant lesion. The Hadamard image shows the extent and characteristics of the border of the lesion whereas the lesion is barely visible on the ADC image. The delineation of extent and characteristics of the border enables improved discrimination and assessment by the expert radiologist and/or the computer-aided-diagnosis system. Cells within the core of the lesion are densely packed and appear brighter than background tissue on the Hadamard image and darker than background tissue on the ADC image. If breast tissue adjacent to the lesion has intensity midway between the brightness of the core of the lesion and the brightness of the background, it may indicate that malignant cells have leaked into the adjacent tissue; in FIG. 2, this is seen in the Hadamard image but not in the ADC image.

The present invention thus provides a method and system for obtaining diagnostic information from diffusion scan data that can be used, either by itself or in conjunction with ADC, FA, and possibly other diffusion scan data measures, to improve diffusion scan data effectiveness as an adjunct or alternative procedure to DCE for discrimination of malignant lesions from benign conditions.

The long-range potential for breast diffusion imaging goes beyond serving as an adjunct to DCE: Early results indicate that diffusion imaging may be as effective for troublesome non-mass lesions, such as are found in infiltrating lobular carcinoma (ILC) and DCIS [Partridge, S C, DeMartini W B, Kurland B F, Eby P R, White S W, Lehman C D. "Quantitative Diffusion-Weighted Imaging as an Adjunct to Conventional Breast MRI for Improved Positive Predictive Value," AJR December 2009; 193:1716-1722], and it is possible that with computer-aided-diagnosis (CAD) utilizing the present invention, diffusion imaging may have similar (or better) sensitivities and specificities for these or other specific types of cancer or for specific groups or sets of patients. For example, the present invention may have improved sensitivity and/or specificity when used for women with dense breasts when compared to mammography, the current standard or practice.

The present invention provides a method and system for obtaining diagnostic information from diffusion scans that can be used, either by itself or in conjunction with ADC, FA, and possibly other measures, as an alternative to DCE for diagnosing, detecting and/or monitoring certain forms of breast cancer. Using diffusion imaging as an alternative procedure to DCE provides significant morbidity and cost advantages. The lack of contrast agent and reduction in acquisition time would translate into a substantial savings in cost. Moreover, the lack of need for contrast agent would result in reduced morbidity and increased availability to those who are in danger of adverse reaction to the enhancing agent. Diffusion imaging offers the potential for characterizing, at low cost and without contrast, the state of known malignancies that are undergoing therapy, providing a cost-effective method for monitoring the effectiveness of therapy. The present invention improves the sensitivity and/or specificity of diffusion imaging so that it can achieve the performance required for clinical acceptance.

The present invention provides a method and a device for identifying regions on an ADC map or Hadamard image generated from diffusion scan data that may be cancerous and producing parameters reflecting the likelihood that those regions are cancerous, where the obtained parameters provide information that is supplementary and/or complementary to diagnostic information obtained from the magnitude of the ADC and FA values derived from the diffusion scan data and where the parameters so derived are related to the gradients along the margins of regions of the ADC map or Hadamard image the pixels of which are lower or higher in magnitude than the values in the background and/or non-lesion portions of the image. It is understood that the present invention is described in terms of the normal ADC map in which regions of low intensity represent areas of suspicion, but can be similarly applied to modified ADC maps such as, for example, intensity inverted ADC maps, in which areas of suspicion are indicated by high pixel intensity, by appropriately modifying the algorithm to correspond to the modification to the ADC map. For the example of the intensity inverted ADC map, the words "lower" and "higher" in the description would be interchanged, as appropriate. Similarly, the present invention is applied to a Hadamard image in which regions of high intensity represent areas of suspicion, but can be similarly applied to modified Hadamard images such as, for example, intensity inverted Hadamard images, in which areas of suspicion are indicated by low pixel intensity.

To accomplish this result, the present invention is characterized by a method and a device for identifying regions of the ADC maps having values that are lower in magnitude than the background and/or non-lesion portions or regions of the Hadamard image having values that are higher in magnitude than the background and/or non-lesion portions by: defining a margin zone around the identified region; computing the gradient within the margin zone; computing a measure of likelihood of malignancy of a region defined by the margin zone, for example the region formed by pixels surrounded by the margin zone; and using the likelihood measure as input to either a device that displays the likelihood measure to the end user or as input of the likelihood measure for additional computer processing.

Figure 3:
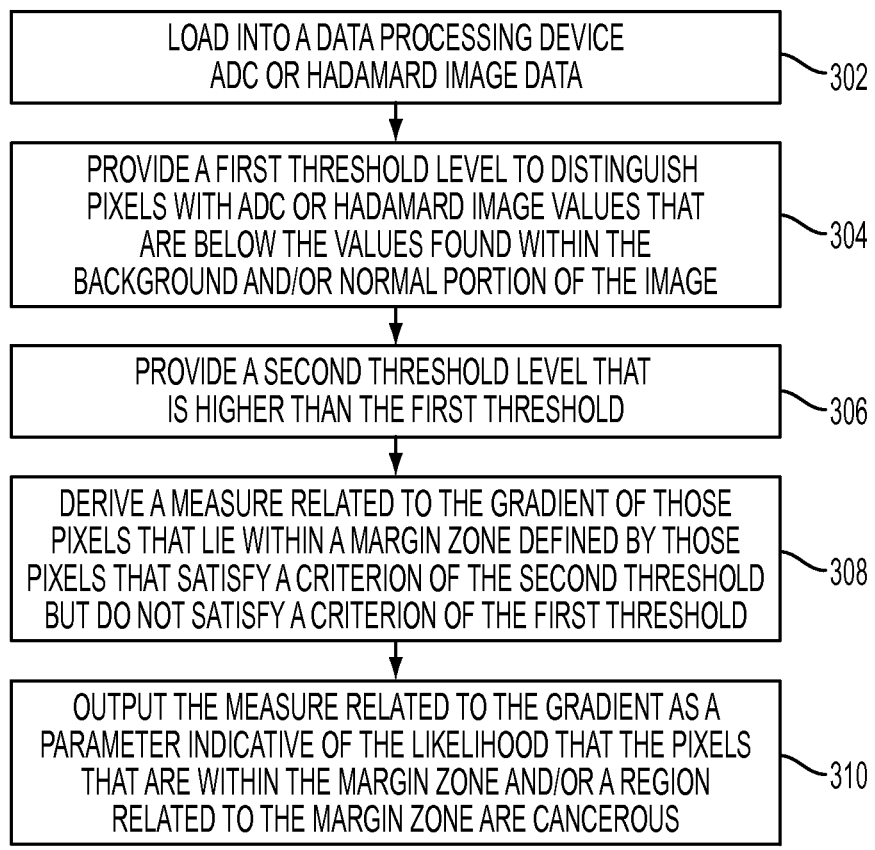
FIG. 3 is a programming diagram showing the basic steps according to the invention for analyzing a lesion based on a parameter of the margin of the lesion.

This identifying method may comprise the following steps, which are depicted in FIG. 3:

(1) Loading an ADC image achieved by calculation from diffusion scan data or loading a Hadamard image generated according to this invention (block 302).

(2) Selecting a first threshold level to distinguish pixels with ADC values that are below the values found within the background and/or normal portion of the image or pixels with Hadamard values that are above the values found within the background and/or normal portion of the image (block 304);

(3) Selecting a second threshold level that is higher than the first threshold level in the case of the ADC map or lower than the first threshold level in the case of the Hadamard image (block 306);

(4) Deriving a measure related to the gradient of those pixels that lie within a margin zone defined by one or more connected sets of pixels that satisfy a criterion of the second threshold but do not satisfy a criterion of the first threshold (block 308), where the criteria for the two thresholds may be either of the pair $\{<, \leq\}$, or the pair $\{>, \geq\}$, for example, pixels in the margin zone may consist of a connected set of pixels that have intensity values less than or equal to the second threshold and are not less than the first threshold in the case of ADC, or a set of pixels that may, for example, have intensity values greater than the second threshold and less than or equal to the first threshold in the case of Hadamard image, and the measure related to the gradient may be a step function monotonically related to the gradient as described in Methods of Achieving Step 4, below.

(5) Outputting the measure related to the gradient as a parameter reflective of the likelihood that the pixels that are within the margin zone and/or a region related to the margin zone are cancerous (block 310).

Multiple methods exist and are known to practitioners in the field for achieving each of steps (1) through (5). The invention comprises a method and device that uses these 5 steps to achieve the objective of providing additional diagnostic indicators of suspicion of cancer on maps or images derived from diffusion scan data.

For illustrative purposes, two methods of achieving each of steps (1) through (5) will be described. It is to be understood that these methods do not restrict the invention and that similar and/or comparable methods known to practitioners in the field can be used.

Methods of achieving step (1): Loading ADC maps or Hadamard images achieved by calculation from diffusion scan data.

Method 1A of achieving step (1): Loading an ADC map into data processing device, such as a computer, from an external source, such as a post-processing module integrated into the MRI system or computing a Hadamard image according to the invention and loading the Hadamard image into data processing device.

Method 1B of achieving step (1): Computing eigenvalues from the diffusion scan data and generating ADC values from the eigenvalues using known mathematical methods and loading the ADC values into the data processing device.

Methods of achieving step (2): Setting a first threshold level to distinguish pixels with ADC values that are below or above the values found within the background and/or normal portion of the image or to distinguish pixels with Hadamard image values that are above or below the values found within the background and/or normal portion of the image.

Method 2A of achieving step (2). The first threshold level is determined on the basis of prior research and clinical knowledge of the physiological application and diffusion imaging parameters by the technical and/or medical staff conducting the procedure or maintaining the MRI system.

Method 2B of achieving step (2). The first threshold level is computed from a histogram analysis of the ADC map by identifying pixel values that are statistically lower in value than pixel values found within the organ or background of the image or from a histogram analysis of the Hadamard image by identifying pixel values that are statistically higher in value than pixel values found within the organ or background of the image. For example, the threshold level may be determined to be a fixed number of standard deviation below or above the mean pixel value within the imaged organ.

Methods of achieving step (3): Setting a second threshold level that is higher than the first threshold level in the case of the ADC map or lower than the first threshold level in the case of the Hadamard image Method 3A of achieving step (3) is to select a second threshold level based upon some function of the first threshold level on the scale of possible threshold levels. For example, the second threshold level could be selected to be "N" threshold units above the first threshold level in the case of ADC or below the first threshold in the case of Hadamard image, where "N" is determined from research or clinical experience.

Method 3B of achieving step (3) is to select a second threshold level based on the number or fraction of pixels that satisfy the second threshold criterion when compared to the number of pixels that satisfy the first threshold criterion for pixels lying within a particular body part.

Methods of achieving step (4): Deriving a measure related to the gradient of those pixels that lie within a margin zone defined by those pixels that satisfy the criterion of the second threshold but do not satisfy the criterion of the first threshold, where the criteria may be any of < or ≤;

Method 4A of achieving step (4). A point P=(x0,y0) in an (x,y) plane of the volume region being examined is interior to the margin zone if P and each of its nearest 8 neighbors, {(x0+1,y0), (x0−1,y0), (x0,y0+1), (x0,y0−1), (x0+1,y0+1), (x0+1,y0+1), (x0−1,y0+1), (x0+1,y0+1)}, is also within the margin zone. For each point P interior to the margin zone, find the maximum ADC values at {(x0+1,y0), (x0−1,y0), (x0,y0+1), (x0,y0−1)} and denote those values by Max_4(P). Find the maximum ADC values at {(x0+1,y0+1), (x0+1,y0+1), (x0−1,y0+1), (x0+1,y0+)} and denote it by Max_8(P). Let ADC(P) be the ADC value at point P. The ADC gradient at P is the maximum of Max_4(P)−ADC(P) and Max_8(P)−ADC(P)/1.414. Let the measure related to the gradient of pixels that lie within the margin zone be computed as the mean of the distribution of gradient values within the interior of the margin zone.

Method 4B of achieving step (4) is the method of expanding geometric regions-of-interest, as implemented in the step function method, described in U.S. Patent Application Publication No. 2009/0060297 (corresponding to U.S. Pat. No. 7,974,676), incorporated herein by reference, and particularly paragraphs [0039] through [0041] of the published application, reproduced below. An example of a method for defining the landmark is to have a radiologist draw a region-of-interest (ROI) in the approximate location of the lesion and use the pixel with the lowest intensity in the case of the ADC map or the highest intensity in the case of the Hadamard image as the landmark. An example of the ending criterion is where the number of pixels in the grown cluster first achieves a minimum of a multiple "N" times the number of pixels in the initial cluster corresponding to the first threshold, where N is an integer such as "4".

Using standard thresholding and clustering algorithms, a cluster is grown around the landmark for each possible intensity value, which according to one embodiment starts with the highest (e.g., 255) and ending with the lowest (0). The clusters around the landmark form a nested, monotonically increasing (but not necessarily strictly increasing) sequence. At each possible intensity level, a region-of-interest (ROI) is constructed around the cluster in a particular shape such that the ROI is the minimal shape containing the cluster. According to one embodiment, the ROI is a minimal rectangular box, or rectangular hull formed around the cluster. Other shapes may be used within the skill of the ordinary artisan. The ROIs also form a nested, monotonically increasing (but not necessarily strictly increasing) sequence. According to one embodiment of the present invention, where the ROI is a rectangular box, for each ROI in the sequence, we compute the area of the ROI by multiplying width by height. If the shape for the ROI is not a rectangular box, the area is computed using a different formula, depending on the ROI shape. If the characterization of the ROI being used is not the area, then a different formula may be used. As an example of a possible characterization other than area, in ultrasound, the ratio of width to height is important and this ratio can be used as the chosen characteristic. Further, if the ROI is depicted in 3-dimensions, instead of 2-dimensions, volume of the ROI may be used instead of area.

A plot of ROI area vs. intensity level is a step function—the plot of ROI area vs. intensity may remain constant for several intensity levels and then "step" up to a larger size. The number of steps has been found to be highly predictive of whether the lesion is benign or malignant using images from a variety of MRI imaging systems and protocols. Moreover, the number of steps has been found to show a high degree of independence from other discriminatory features and to be useful as a component of a computer-aided-diagnosis or computer-aided-detection system. In the specific example shown here, an image of a lesion is interpreted as being benign if the number of steps is less than or equal to 9 and is interpreted as being cancer if the number of steps is greater than 9. These thresholds may be adjusted as appropriate by an ordinarily skilled artisan. Additionally, other numbers related to the characterization of the ROI may be used.

While the number of distinct ROIs is a function of shape and gradient of a lesion, it is relatively insensitive to transformations of intensity values, such as windowing and leveling, provided that these transformations are not extreme (e.g., the leveling cannot have reduced the image to a few intensities).

Methods of achieving step (5): outputting the measure related to the gradient as a parameter reflective of the likelihood that the pixels that are within the margin zone and/or the identified region from which the margin zone was defined, as described above, are cancerous.

Method 5A of achieving step (5): The output of the gradient measure is displayed to the user in the form of a numeric value, a color code, or a marker such as "x" superimposed on the ADC map or Hadamard image on an image display.

Method 5B of achieving step (5): The output of the gradient measure is input to a processor that combines the output gradient measure with one or more other measures of suspicion derived from the values diffusion scans to compute a new measure of suspicion.

Figure 4:
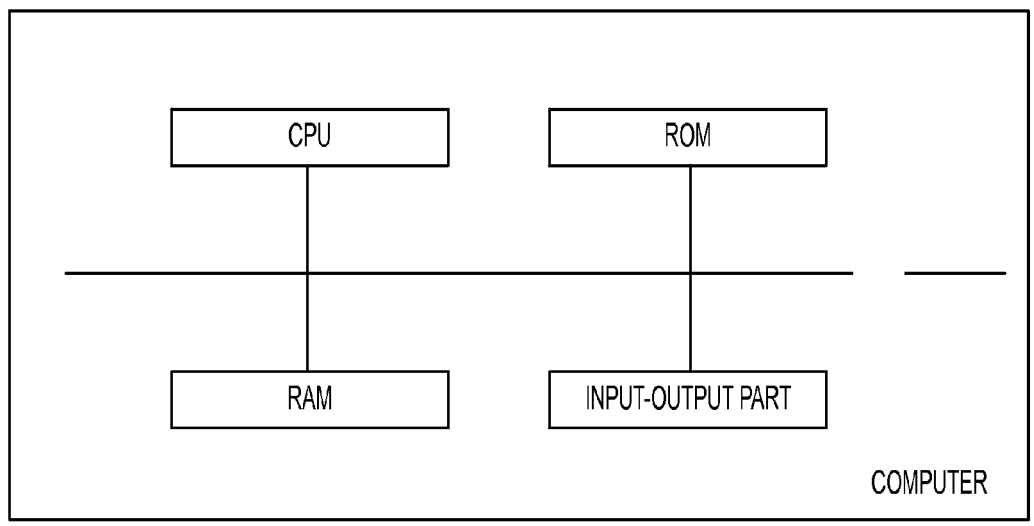
FIG. 4 is a block diagram of the essential components of a general purpose computer that may be used to practice the present invention.

FIG. 4 is a block diagram of a general purpose computer that may be used to carry out the processing operations according to the present invention. The computer comprises a CPU, a RAM, a ROM, and an input-output part, which are connected to one another through a bus. The input-output part may include a keyboard, a display, possibly with a touch screen, a printer, a data input configured to be coupled to an MRI apparatus, and a wireless link. Software, or a program, for implementing the invention is stored in non-transitory form in the ROM and is executed under control of the CPU. Data obtained by the scanning operations and computation results are stored in the RAM and the computation results are provided to a suitable output device, for example the display and/or printer.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for generating a map of a region of a patient's body that provides information about the nature of lesion(s) in the region, the region being composed of a two or three dimensional matrix of elemental subregions, said method comprising:

performing at least one first scan of the region with an MRI apparatus set to a first b value, $B_1$, to obtain a first matrix of pixel or voxel intensity values, each intensity value of the first matrix being designated int $(B_1)$, and each intensity value of the first matrix being derived from a respective subregion; performing at least one second scan of the region with the MRI apparatus set to a second b value, $B_2$, to obtain a second matrix of pixel or voxel intensity values, each intensity value of the second matrix being designated int $(B_2)$, and each intensity value of the second matrix being derived from a respective subregion;

deriving, for each subregion that is the same subregion scanned in the first and second scans, a first computed value that is a logarithmic function of (int $(B_1)$/int$(B_2)$) or a monotonic function of ln (int $(B_1)$/int$(B_2)$);

multiplying each first computed value by a value proportional to int $(B_1)$ for the same subregion to obtain a second computed value for each subregion; and producing a representation of all the second computed values.

2. The method of claim 1, wherein each at least one scan comprises one scan performed for the first b value, $B_1$, where $B_1$ is equal to 0 and N scans performed in N different directions for the second b value, $B_2$, where $B_2$ is greater than 0, where N is an integer greater than 1, and said deriving comprises deriving matrices of pixel values, int$(B_1)$ and int$(B_2)$ for each of the N scans.

3. The method of claim 1, where each at least one scan comprises N scans performed in N different directions for a first b value, $B_1$, where $B_1$ is greater than 0 and N scans performed in N different directions for a second b value, $B_2$, where $B_2$ is greater than 0, where N is an integer great than 1, and said deriving comprises deriving matrices of pixel values int$(B_1)$ and int$(B_2)$ for each of the N scans.

4. The method of claim 1, wherein each at least one scan consists of only one scan.

5. The method of claim 1, wherein each at least one scan consists of at most 2 scans.

6. The method of claim 1, wherein the representation of the second computed values contains an indication of level of suspicion of cancer for one or more body subregions.

7. The method of claim 1, wherein the second computed value is independent of the presence or absence of a contrast agent.

8. The method of claim 1, wherein the scans are performed while the region of the patient's body is free of contrast agent.

9. The method of claim 1, wherein the region of the patient's body consists of at least a portion of a breast.

* * * * *